United States Patent
Inada et al.

(10) Patent No.: US 11,313,861 B2
(45) Date of Patent: Apr. 26, 2022

(54) METHOD OF EVALUATING HEPATIC GLUCOSE UPTAKE CAPACITY

(71) Applicants: OTSUKA PHARMACEUTICAL CO., LTD., Tokyo (JP); TOHOKU UNIVERSITY, Sendai (JP)

(72) Inventors: Makoto Inada, Tokushima (JP); Keiko Kawata, Tokushima (JP); Kimiyoshi Sudoh, Takarazuka (JP); Hideki Katagiri, Sendai (JP); Tetsuya Yamada, Sendai (JP); Kei Takahashi, Sendai (JP)

(73) Assignees: OTSUKA PHARMACEUTICAL CO., LTD., Tokyo (JP); TOHOKU UNIVERSITY, Sendai (JP)

( * ) Notice: Subject to any disclaimer, the term of this patent is extended or adjusted under 35 U.S.C. 154(b) by 0 days.

(21) Appl. No.: 16/348,751

(22) PCT Filed: Nov. 10, 2017

(86) PCT No.: PCT/JP2017/040585
§ 371 (c)(1),
(2) Date: Jul. 10, 2019

(87) PCT Pub. No.: WO2018/088521
PCT Pub. Date: May 17, 2018

(65) Prior Publication Data
US 2019/0324016 A1 Oct. 24, 2019

(30) Foreign Application Priority Data

Nov. 11, 2016 (JP) .............................. JP2016-220510

(51) Int. Cl.
| | |
|---|---|
| *G01N 33/66* | (2006.01) |
| *A61K 51/12* | (2006.01) |
| *A61B 5/083* | (2006.01) |
| *G01N 33/50* | (2006.01) |
| *A61B 5/08* | (2006.01) |
| *A61K 49/00* | (2006.01) |
| *G01N 33/497* | (2006.01) |
| *G01N 33/60* | (2006.01) |

(52) U.S. Cl.
CPC .......... *G01N 33/66* (2013.01); *A61B 5/0836* (2013.01); *G01N 33/5038* (2013.01); *A61B 5/0813* (2013.01); *A61K 49/00* (2013.01); *A61K 51/1206* (2013.01); *G01N 33/497* (2013.01); *G01N 33/60* (2013.01); *G01N 2800/042* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 5,916,538 A | 6/1999 | Kohno et al. | |
| 6,071,245 A | 6/2000 | Kohno et al. | |
| 10,393,730 B2 * | 8/2019 | Inada ................. | A61B 5/083 |
| 2003/0044993 A1 | 3/2003 | Yatscoff et al. | |
| 2015/0204852 A1 | 7/2015 | Inada et al. | |

FOREIGN PATENT DOCUMENTS

| | | |
|---|---|---|
| EP | 2 887 066 A1 | 6/2015 |
| JP | 10-067689 A | 3/1998 |
| JP | 11-171798 A | 6/1999 |
| JP | 2002-513911 A | 5/2002 |
| JP | 2008-292506 A | 12/2008 |
| JP | 5901092 B1 | 4/2016 |
| WO | 99/56790 A1 | 11/1999 |
| WO | 2012/037603 A1 | 3/2012 |
| WO | 2014/030650 A1 | 2/2014 |

OTHER PUBLICATIONS

Loria et al. Liver and diabetes. A vicious circle. 2013 Hepatol. Res. 43: 51-64. (Year: 2013).*
Dillon et al. Novel noninvasive breath test method for screening individuals at risk for diabetes. 2009 Diabetes Care 32: 430-435. (Year: 2009).*
Kristina Blaslov et al., "Incretin based therapies: A novel treatment approach for nonalcoholic fatty liver disease", World Journal of Gastroenterology, Jun. 21, 2014, pp. 7356-7365, vol. 20, No. 23.
International Search Report of PCT/JP2017/040585 dated Jan. 9, 2018 [PCT/ISA/210].
International Preliminary Report on Patentability of PCT/JP2017/040585 dated May 14, 2019.
Perreault et al., "Approaching Pre-diabetes", Journal of Diabetes and Its Complications, vol. 28, No. 2, 2014, pp. 226-233.
Bansal, "Prediabetes diagnosis and treatment: A review", World Journal of Diabetes, vol. 6, No. 2, Mar. 15, 2015, pp. 296-303.
Partial Supplementary European Search Report dated May 19, 2020 by the European Patent Office in EP application No. 17869074.9.

* cited by examiner

*Primary Examiner* — Jennifer Lamberski
(74) *Attorney, Agent, or Firm* — Sughrue Mion, PLLC

(57) ABSTRACT

An object of the disclosure is to provide a composition for evaluating the hepatic glucose uptake capacity of a subject and a method for evaluating the hepatic glucose uptake capacity of a subject with the composition. An object of the disclosure is to provide a method for determining the stage of pre-onset diabetes in a subject with pre-onset diabetes using the method for evaluating the hepatic glucose uptake capacity. An aspect of the disclosure accordingly provides a composition comprising $^{13}C$-labeled glucose for evaluating the hepatic glucose uptake capacity of a subject. Another aspect of the disclosure provides a method comprising measuring $^{13}C$-labeled glucose in a blood sample or an expired air sample obtained from the subject to which the composition was administered. The desired evaluation or determination can be achieved by comparing the measured value with a reference value.

10 Claims, 8 Drawing Sheets

$C_{in}$ = inlet concentration
$C_{out}$ = outlet concentration
$Q$ = blood velocity $Q_{portal} = 4\, Q_{h.artery}$
$Q_h = 5\, Q_{h.artery}$ inlet velocity $(V_{in}) = 4\, Q_{h.artery} \times C_{in\, portal} + Q_{h.artery} \times C_{in\, h.artery}$ outlet velocity $(V_{out}) = 5\, Q_{h.artery} \times C_{out}$ Hepatic Extraction Ratio $\quad E_h \;=\; \dfrac{V_{in} - V_{out}}{V_{in}}$

METHOD OF EVALUATING HEPATIC GLUCOSE UPTAKE CAPACITY

CROSS REFERENCE TO RELATED APPLICATIONS

This application is a National Stage of International Application No. PCT/JP2017/040585 filed Nov. 10, 2017, claiming priority to Japanese Patent Application No. 2016-220510 filed Nov. 11, 2016, the contents of both of which are incorporated herein by reference in their entirety.

TECHNICAL FIELD

The disclosure relates to a composition for evaluating a hepatic glucose uptake capacity and a method for evaluating a hepatic glucose uptake capacity with the composition.

BACKGROUND ART

Metabolic diseases, e.g., diabetes, have been a social problem all over the world. Diagnosis of metabolic diseases that enables early detection has been desired from the viewpoint of preventive medicine.

The liver plays a key role in energy metabolism in the body. For example, the liver takes up glucose ingested via meals, converts glucose into glycogen, stores glycogen, and decomposes glycogen to supply glucose to blood when required. The regulation of the hepatic glucose uptake is known to get damaged before onset or in early phase of some metabolic diseases, e.g., diabetes. Detecting the abnormal regulation has been considered promising for early diagnosis of the diseases, but such detection has not been achieved by evaluating the hepatic glucose uptake capacity.

Various evaluation methods have been developed for early detecting metabolic diseases such as diabetes. For example, a so-called labeled-C breath test has been proposed for diabetic diagnosis, in which $^{13}C$-labeled glucose is administered to a patient and $^{13}CO_2$ discharged in the expired air is measured (see Patent Literatures 1 to 4). Patent Literature 1 specifically describes a method of diagnosing diabetes and its type (type 1 or 2) comprising performing a breath test using glucose with a carbon atom at a specific position replaced with $^{13}C$, and measuring the degree of increase of the $^{13}CO_2$ level in the exhalation. Patent Literatures 2 and 3 disclose that diabetes, insulin resistance, or impaired glucose tolerance can be diagnosed by performing a breath test in which $^{13}C$-labeled glucose is used in the same manner as in Patent Literature 1, and determining that the ratio of $^{13}C$ to $^{12}C$ in the exhalation ($^{13}C/^{12}C$) derived from the $^{13}CO_2$ level in the exhalation is lower than that of healthy people. Patent Literature 4 discloses that the disease stage of diabetes can be determined by measuring a glucose metabolism ability of a patient using a labeled C breath test.

REFERENCES

Patent Literature

[Patent Literature 1] JP-A-H10-67689
[Patent Literature 2] JP-A-2002-513911
[Patent Literature 3] JP-A-2008-292506
[Patent Literature 4] WO2014/030650

SUMMARY OF THE INVENTION

An object of the disclosure is to provide a composition for evaluating the hepatic glucose uptake capacity of a subject and a method for evaluating the hepatic glucose uptake capacity of a subject with the composition. An object of the disclosure is to provide a method for determining the stage of pre-onset diabetes in a subject with pre-onset diabetes by using the method for evaluating the hepatic glucose uptake capacity.

The inventors have found that the hepatic glucose uptake capacity of a subject can be evaluated by administering $^{13}C$-labeled glucose to the subject and observing its behavior.

An aspect of the disclosure accordingly provides a composition comprising $^{13}C$-labeled glucose for evaluating the hepatic glucose uptake capacity of a subject.

An aspect of the disclosure provides a method of evaluating the hepatic glucose uptake capacity of a subject, comprising:
(1) measuring the $^{13}C$-labeled glucose level in a blood sample obtained from the subject to which $^{13}C$-labeled glucose was orally administered; and
(2) comparing the level with a reference value to evaluate the hepatic glucose uptake capacity (hereinafter referred to as Method (I)).

An aspect of the disclosure provides a method of evaluating the hepatic glucose uptake capacity of a subject, comprising:
(1) calculating the ratio of the $^{13}CO_2$ amount to the unlabeled $CO_2$ amount or total $CO_2$ amount in an expired air sample obtained from the subject to which $^{13}C$-labeled glucose was intravenously administered;
(2) calculating the ratio of the $^{13}CO_2$ amount to the unlabeled $CO_2$ amount or total $CO_2$ amount in an expired air sample obtained from the subject to which $^{13}C$-labeled glucose was orally administered;
(3) calculating the difference between the ratio calculated in step (1) and the ratio calculated in step (2); and
(4) evaluating the hepatic glucose uptake capacity based on the difference calculated in step (3)
(hereinafter referred to as Method (II)).

An aspect of the disclosure provides a method of determining the stage of pre-onset diabetes in a subject with pre-onset diabetes, comprising:
(1) measuring the $^{13}C$-labeled glucose level in a blood sample obtained from the subject to which $^{13}C$-labeled glucose was orally administered; and
(2) comparing the level with a reference value to determine the stage of pre-onset diabetes is stage A or stage B (hereafter referred to as Method (III)).

The disclosure enables evaluating the hepatic glucose uptake capacity of a subject. Such evaluation may facilitate diagnosis of metabolic diseases, e.g., diabetes, and may contribute to preventive medicine.

DETAILED DESCRIPTION

Figure 1:
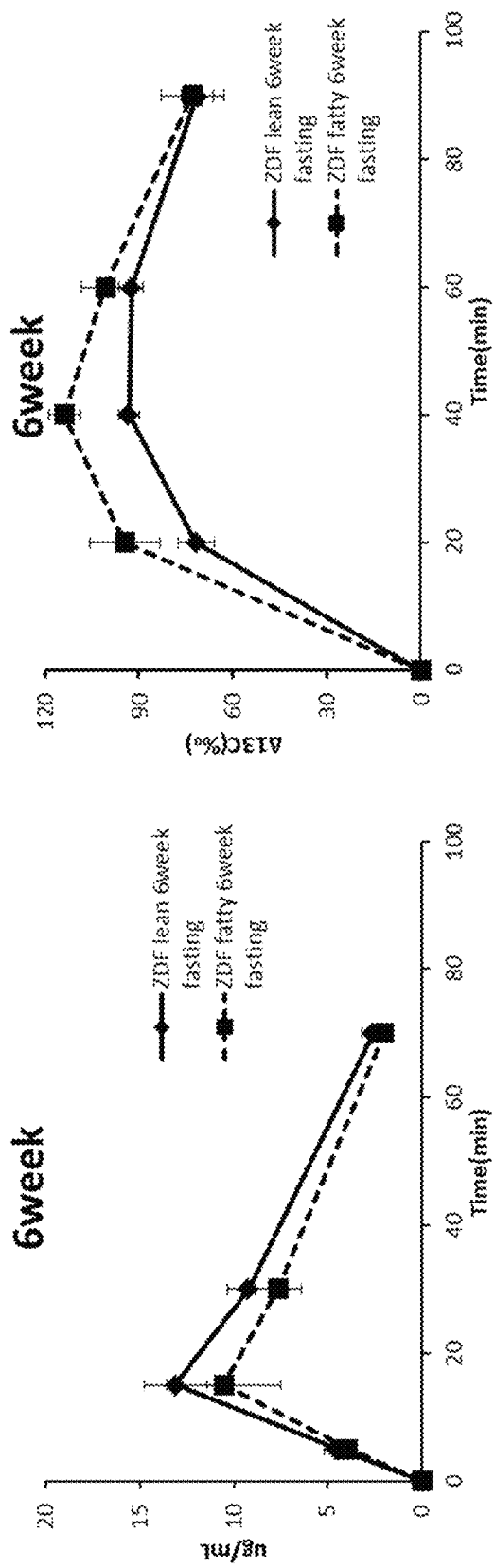
FIG. 1 shows the blood $^{13}C$-glucose levels and the $\Delta^{13}C$ values of the expired air in 6-week-old ZDF fatty rats and ZDF lean rats to which $^{13}C$-glucose was administered.

Unless otherwise defined, the terms used herein are read as generally understood by a skilled person in the technical fields such as organic chemistry, medicine, pharmacology, molecular biology, and microbiology. Several terms used herein are defined as described below. The definitions herein take precedence over the general understanding.

When a numerical value is accompanied with the term "about", the value is intended to represent any value within the range of ±10% of that value. A numerical range covers all values from the lower limit to the upper limit and includes the values of the both limits. When a numerical range is accompanied with the term "about", the both limits are read as accompanied with the term. For example, "about 20 to 30" is read as "20±10% to 30±10%."

Composition Comprising $^{13}C$-Labeled Glucose

An aspect of the disclosure provides a composition comprising $^{13}C$-labeled glucose for evaluating the hepatic glucose uptake capacity of a subject. The $^{13}C$-labeled glucose is labeled in a manner such that at least a portion of the $CO_2$ formed through the glucose metabolic pathway is labeled with $^{13}C$. Examples of such glucose include glucose in which at least a carbon atom at the 1- or 6-position, the 2- or 5-position, and the 3- or 4-position is $^{13}C$. Specific examples include 1-$^{13}C$-labeled glucose, 2-$^{13}C$-labeled glucose, and 3-$^{13}C$-labeled glucose. Some or all of the carbon atoms at the 1-, 2-, 3-, 4-, 5-, and 6-positions of glucose may be $^{13}C$. In an embodiment, glucose in which the carbon atom at the 3- or 4-position is $^{13}C$ or glucose in which all of the carbon atoms at the 1-, 2-, 3-, 4-, 5-, and 6-positions are $^{13}C$ are used, because $^{13}C$ administered as the $^{13}C$-labeled glucose is rapidly excreted into the expired air in the form of $^{13}CO_2$.

Glucose may be $^{13}C$-labeled by any of the commonly used methods without limitation (e.g., Sasaki, "5.1 Antei Doitai no Rinsho Shindan heno Oyo [5.1 Application of Stable Isotopes in Clinical Diagnosis]," Kagaku no Ryoiki [Journal of Japanese Chemistry] 107, pp. 149-163 (1975), Nankodo; Kajiwara, RADIOISOTOPES, 41, 45-48 (1992)). Any commercially available $^{13}C$-labeled glucose also may be used.

The features of the composition, such as the form, components other than the $^{13}C$-labeled glucose, proportion of each component, and preparation method of the composition, are not limited as long as the $^{13}C$-labeled glucose is absorbed and metabolized in the body, and excreted into the expired air in the form of $^{13}C$-labeled carbon dioxide.

For example, the form of the composition may be an oral dosage form or an intravenous dosage form. Examples of oral dosage forms include any oral dosage forms, for example liquids such as solutions (including syrup), suspensions, and emulsions; and solids such as tablets (with or without coating), chewable tablets, capsules, pills, pulvis (powders), fine particles, and granules. Examples of intravenous dosage forms include dosage forms such as injections and drops (in liquid, suspension, or emulsion form). In an embodiment, the composition is in the form of an oral dosage form. In another embodiment, the composition is in the form of an intravenous dosage form.

The form of the composition is not limited to pharmaceutical dosage forms. The composition may be in any form as long as it contains the $^{13}C$-labeled glucose and does not adversely affect the effects of the composition. For example, $^{13}C$-labeled glucose described above may be combined with any foodstuff and formed into solid food, fluid food, or liquid food.

The composition may substantially consist of $^{13}C$-glucose described above. Alternatively, as long as the effects of the composition are not adversely affected, any pharmaceutically acceptable carrier or additive that is generally used in the field may be added in accordance with each pharmaceutical form (dosage form).

The amount of $^{13}C$-labeled glucose contained in the composition is not limited. For example, the amount of $^{13}C$-labeled glucose may be suitably adjusted in the range of 1 to 99 wt % based on the total weight (100 wt %) of the composition. For example, the amount of the $^{13}C$-labeled glucose contained in the composition may be conveniently adjusted so that the single dose in a method described below is in a suitable range.

When the composition is prepared in a liquid, suspension, or emulsion form, for example, drops or injections, various carriers and/or additives suitable for such forms, as well as purified water or water for injection, may be used. Commonly used additives may be used, for example, isotonic agents (e.g., sodium chloride), pH adjusters (e.g., hydrochloric acid, sodium hydroxide), buffers (e.g., boric acid, sodium monohydrogen phosphate, sodium dihydrogen phosphate), preservatives (e.g., benzalkonium chloride), and thickeners (e.g., carboxyvinyl polymers).

When the composition is formed into a solid form, for example, tablets, chewable tablets, capsules, pills, pulvis (powders), fine particles, and granules, various carriers and/or additives suitable for such forms may be used.

Examples of carriers or additives include excipients, such as lactose, sucrose, dextrin, mannitol, xylitol, sorbitol, erythritol, calcium dihydrogen phosphate, sodium chloride, glucose, urea, starch, calcium carbonate, kaolin, crystalline cellulose, and silicic acid; binders, such as water, ethanol, simple syrup, glucose liquid, starch liquid, gelatin liquid, carboxymethyl cellulose, sodium carboxymethyl cellulose, shellac, methyl cellulose, hydroxypropylmethyl cellulose, hydroxypropyl cellulose, potassium phosphate, polyvinyl alcohol, polyvinyl pyrrolidone, dextrin, and pullulan; disintegrators, such as dry starch, sodium alginate, agar powder, laminaran powder, sodium bicarbonate, calcium carbonate, polyoxyethylene sorbitan fatty acid esters, sodium lauryl sulfate, monoglyceride stearate, starch, lactose, carmellose calcium, low substituted hydroxypropyl cellulose, carmellose, croscarmellose sodium, sodium carboxymethyl starch, and crospovidone; disintegration inhibitors, such as sucrose, stearic acid, cacao butter, and hydrogenated oil; absorption promoters, such as polysorbate 80, quaternary-ammonium base, and sodium lauryl sulfate; humectants, such as glycerin and starch; adsorbents, such as starch, lactose, kaolin, bentonite, and colloidal silicic acid; lubricants, such as purified talc, stearate, boric acid powder, polyethylene glycol, colloidal silicic acid, sucrose fatty acids, and hardened oil; pH adjustors, such as citric acid, anhydrous citric acid, sodium citrate, sodium citrate dihydrate, anhydrous sodium monohydrogenphosphate, anhydrous sodium dihydrogenphosphate, and sodium hydrogen phosphate; coloring agents, such as iron oxide, beta-carotene, titanium oxide, food colors, copper chlorophyll, and riboflavin; and corrigents, such as ascorbic acid, sodium chloride, and various sweeteners.

Tablets may be provided with an ordinary coating, if necessary. Examples of such tablets include sugar-coated tablets, gelatin-coated tablets, film-coated tablets, double-coated tablets, and multi-coated tablets. Capsules may be prepared in a commonly used method, e.g., by mixing $^{13}$C-labeled glucose with any of various carriers mentioned above and placing it in capsules such as hard gelatin capsules or soft capsules.

Method (I)

The composition may be used in Method (I): a method of evaluating the hepatic glucose uptake capacity of a subject, comprising
(1) measuring the $^{13}$C-labeled glucose level in a blood sample obtained from the subject to which $^{13}$C-labeled glucose was orally administered; and
(2) comparing the level with a reference value to evaluate the hepatic glucose uptake capacity.

As to Method (I), the "subject" may be any mammal. Examples thereof include humans and mammals other than humans. Examples of the mammals other than humans include mice, rats, guinea pigs, rabbits, dogs, cats, monkeys, swine, bovines, and horses, and preferable examples thereof include mice, rats, guinea pigs, rabbits, dogs, and monkeys. In an embodiment, the subject is a human, a rat, or a mouse.

As to Method (I), the subject may be healthy, or may have a disease, for example, a metabolic disease. The term "healthy" means that any sign and/or symptom of diseases is not observed in the subject. Examples of the metabolic diseases include liver diseases, such as non-alcoholic steatohepatitis (NASH), non-alcoholic fatty liver disease (NAFLD), a fatty liver, viral hepatitis (e.g., hepatitis B or hepatitis C), alcoholic liver disease, primary biliary cirrhosis, primary sclerosing cholangitis, hemochromatosis, autoimmune hepatitis, and liver cirrhosis; diabetes; prediabetes such as borderline diabetes; insulin resistance; hyperglycemia; hyperinsulinemia; obesity; dyslipidemia, and high blood pressure. The subject may be a subject suspected of having any of these diseases.

As to Method (I), the subject may be fasted or unfasted immediately before the administration of $^{13}$C-labeled glucose. For example, the subject may be fasted, e.g., for at least 2 hours, preferably for at least 4 hours, immediately before the administration of $^{13}$C-labeled glucose, with freely ingesting water. When the subject is unfasted immediately before the administration of $^{13}$C-labeled glucose, usual diet may be ingested as usual.

As to Method (I), the term "hepatic glucose uptake capacity" means the capacity of the liver to take up orally ingested glucose. The liver supplies glucose to the hepatic vein blood at the time of hunger, whereas takes up glucose from the portal vein blood and reduces glucose supply to the hepatic vein blood at the time of nutritional intake, thereby maintaining the blood glucose level constant. The amount of glucose taken up into the liver is therefore the amount obtained by subtracting the amount of glucose supplied to the hepatic vein blood from the amount of glucose taken up from the portal vein blood. As to Method (I), the term "decreased hepatic glucose uptake capacity" means that the amount of glucose taken up into the liver is decreased.

Step (1) of Method (I) measures the $^{13}$C-labeled glucose level in a blood sample obtained from the subject to which $^{13}$C-labeled glucose was orally administered. As to Method (I), the amount of $^{13}$C-labeled glucose administered to the subject can be appropriately adjusted. For example, when the subject is a human (adult), it can be adjusted in the range of 5 mg/body to 50 g/body, preferably 10 mg/body to 25 g/body.

As to Method (I), the blood sample may be obtained from the subject at any time point "t" after the administration of $^{13}$C-labeled glucose. In other words, the blood sample may be obtained after the duration from the administration of $^{13}$C-labeled glucose to a time point "t". As to Method (I), the time point "t" is also referred to as blood collection time "t".

Those skilled in the art can determine the blood collection time "t" appropriately. For example, any time point in the range of 5 minutes to 360 minutes after the administration of $^{13}$C-labeled glucose may be selected. For example, the blood collection time "t" may be determined by orally administering $^{13}$C-labeled glucose to a mammal of the same species, collecting blood samples at plural time points, measuring the levels of $^{13}$C-labeled glucose in the samples, and selecting the time point at which the level is high. For example, the blood collection time "t" for a rat may be in the range of about 5 to 120 minutes or about 10 to 60 minutes after the administration of $^{13}$C-labeled glucose. For example, the blood collection time "t" for a human may be in the range of about 5 to 240 minutes or about 10 to 120 minutes after the administration of $^{13}$C-labeled glucose. Those skilled in the art can determine the suitable blood collection time "t" for other mammals with reference to these examples.

A blood sample can be obtained from the subject by a commonly used method. The level of $^{13}$C-labeled glucose in a blood sample may be measured by a commonly used procedure, which is well-known to those skilled in the art. For example, the level can be measured using a commonly used analytical technique, such as LS/MS/MS or GC/MS. LC/MS/MS is preferably used.

The area under the curve ($AUC_t$) may be calculated by measuring the levels of $^{13}$C-labeled glucose in blood samples obtained from the subject at plural time points and generating a graph showing change in the level over time. The area under the curve may be calculated according to a commonly used method, which would be easily understood by those skilled in the art. For example, the area under the curve is calculated in a graph showing the change in the level of $^{13}$C-labeled glucose over time, which has the vertical axis showing the level of $^{13}$C-labeled glucose and the horizontal axis showing the elapsed time after the administration of $^{13}$C-labeled glucose. For example, $AUC_{t-0}$ may be calculated in the graph, which is the area under the curve from the administration of $^{13}$C-labeled glucose to the blood collection time "t". For example, $AUC_{t2-t1}$ may be calculated in the graph, which is the area under the curve from the blood collection time "$t_1$" to the blood collection time "$t_2$".

Step (2) of Method (I) compares the level measured in step (1) with a reference value to evaluate the hepatic glucose uptake capacity of the subject. The level at a certain time point or the AUC may be used for the comparison. The level reflects the hepatic glucose uptake capacity of the subject; the higher level indicates that the proportion of glucose taken up into the liver is smaller. The reference value may be derived from the levels measured according to step (1) of Method (I) in a control group, a group of animals of the same species as the subject which have normal hepatic glucose uptake capacities, under the conditions equivalent to those for the subject. The reference value may be obtained simultaneously with, in parallel with, before, or after the measurement of the test value. Alternatively, the reference value may be a value predetermined for each species. Examples of animals having normal hepatic glucose uptake capacities include animals having no metabolic disease, animals in which no abnormality in the liver function is observed by a conventional test method, and animals having no diabetes or pre-onset diabetes such as borderline diabetes. The subject can be determined to have a decreased hepatic glucose uptake capacity when the level measured in step (1) is higher than the reference value.

Method (I) enables the evaluation of the hepatic glucose uptake capacity of the subject. Such evaluation can contribute to the treatment and/or prevention of a disease such as a metabolic disease. Method (I) is also useful for determining the stage of pre-onset diabetes in a subject with pre-onset diabetes, as mentioned below.

An aspect of the disclosure provides a method of evaluating the hepatic glucose uptake capacity of a subject, comprising:
(1) orally administering $^{13}C$-labeled glucose to the subject;
(2) obtaining a blood sample from the subject;
(3) measuring the $^{13}C$-labeled glucose level in the sample; and
(4) comparing the level with a reference value to evaluate the hepatic glucose uptake capacity.

An aspect of the disclosure provides $^{13}C$-labeled glucose for use in evaluating the hepatic glucose uptake capacity of a subject.

An aspect of the disclosure provides use of $^{13}C$-labeled glucose for manufacturing a composition for evaluating the hepatic glucose uptake capacity of a subject.

Method (II)

The composition comprising $^{13}C$-labeled glucose may be used in Method (II): a method of evaluating the hepatic glucose uptake capacity of a subject, comprising:
(1) calculating the ratio of the $^{13}CO_2$ amount to the unlabeled $CO_2$ amount or total $CO_2$ amount in an expired air sample obtained from the subject to which $^{13}C$-labeled glucose was intravenously administered;
(2) calculating the ratio of the $^{13}CO_2$ amount to the unlabeled $CO_2$ amount or total $CO_2$ amount in an expired air sample obtained from the subject to which $^{13}C$-labeled glucose was orally administered;
(3) calculating the difference between the ratio calculated in step (1) and the ratio calculated in step (2); and
(4) evaluating the hepatic glucose uptake capacity based on the difference calculated in step (3).

As to Method (II), the "subject" may be any mammal. Examples thereof include humans and mammals other than humans. Examples of the mammals other than humans include mice, rats, guinea pigs, rabbits, dogs, cats, monkeys, swine, bovines, and horses, and preferable examples thereof include mice, rats, guinea pigs, rabbits, dogs, and monkeys. In an embodiment, the subject is a human, a rat, or a mouse.

As to Method (II), the subject may be healthy, or may have a disease, for example, a metabolic disease. The term "healthy" means that any sign and/or symptom of diseases is not observed in the subject. Examples of the metabolic diseases include liver diseases, such as non-alcoholic steatohepatitis (NASH), non-alcoholic fatty liver disease (NAFLD), a fatty liver, viral hepatitis (e.g., hepatitis B or hepatitis C), alcoholic liver disease, primary biliary cirrhosis, primary sclerosing cholangitis, hemochromatosis, autoimmune hepatitis, and liver cirrhosis; diabetes; prediabetes such as borderline diabetes; insulin resistance; hyperglycemia; hyperinsulinemia; obesity; dyslipidemia, and high blood pressure. The subject may be a subject suspected of having any of these diseases.

As to Method (II), the subject may be fasted or unfasted immediately before the administration of $^{13}C$-labeled glucose. For example, the subject may be fasted, e.g., for at least 2 hours, preferably for at least 4 hours, immediately before the administration of $^{13}C$-labeled glucose, with freely ingesting water. When the subject is unfasted immediately before the administration of $^{13}C$-labeled glucose, usual diet may be ingested as usual.

As to Method (II), the term "hepatic glucose uptake capacity" means the capacity of the liver to take up orally ingested glucose. The liver supplies glucose to the hepatic vein blood at the time of hunger, whereas takes up glucose from the portal vein blood and reduces glucose supply to the hepatic vein blood at the time of nutritional intake, thereby maintaining the blood glucose level constant. The amount of glucose taken up into the liver is therefore the amount obtained by subtracting the amount of glucose supplied to the hepatic vein blood from the amount of glucose taken up from the portal vein blood. As to Method (II), the term "decreased hepatic glucose uptake capacity" means that the amount of glucose taken up into the liver is decreased.

Step (1) of Method (II) calculates the ratio of the $^{13}CO_2$ amount to the unlabeled $CO_2$ amount or total $CO_2$ amount in an expired air sample obtained from the subject to which $^{13}C$-labeled glucose was intravenously administered. Step (2) calculates the ratio of the $^{13}CO_2$ amount to the unlabeled $CO_2$ amount or total $CO_2$ amount in an expired air sample obtained from the subject to which $^{13}C$-labeled glucose was orally administered. The intravenous or oral administration of $^{13}C$-labeled glucose can be achieved by intravenously or orally administering the above-mentioned composition. Preferably an interval of at least 6 hours, for example, 12 hours, 1 day, 2 days, 3 days, 4 days, or 5 days is present between the intravenous administration and the oral administration of $^{13}C$-labeled glucose. Either of step (1) and (2) can be performed earlier.

As to Method (II), the amount of $^{13}C$-labeled glucose administered to the subject can be appropriately adjusted. For example, when the subject is a human (adult), it can be adjusted in the range of 5 mg/body to 50 g/body, preferably 10 mg/body to 25 g/body. The amounts in step (1) and step (2) may be the same or different.

In steps (1) and (2) of Method (II), the expired air samples may be obtained from the subject at any time point "t" after the intravenous or oral administration of $^{13}C$-labeled glucose. In other words, the expired air samples may be obtained after the duration from the administration of $^{13}C$-labeled glucose to a time point "t". The time point "t" is also referred to as expired air collection time "t".

Those skilled in the art can determine the expired air collection time "t" appropriately. For example, any time point in the range of 5 minutes to 240 minutes after the administration of $^{13}C$-labeled glucose may be selected. For example, the expired air collection time "t" may be determined by intravenously or orally administering $^{13}C$-labeled glucose to a mammal of the same species, collecting expired air samples at plural time points, calculating the ratio of the $^{13}CO_2$ amount to the total $CO_2$ amount, and selecting the time point at which the ratio of the $^{13}CO_2$ amount is high. For example, the expired air collection time "t" for a rat may be in the range of about 0 to 120 minutes or about 10 to 60 minutes after the administration of $^{13}C$-labeled glucose. For example, the expired air collection time "t" for a human may be in the range of about 5 to 240 minutes or about 10 to 120 minutes after the administration of $^{13}$C-labeled glucose. Those skilled in the art can determine the suitable expired air collection time "t" for other mammals with reference to these examples.

An expired air sample can be obtained by a conventional method for breath tests known to those skilled in the art. The measurement and analysis of $^{13}$CO$_2$, unlabeled CO$_2$, and total CO$_2$ contained in an expired air sample is known to those skilled in the art and may be performed by a commonly used analysis method. For example, $^{13}$CO$_2$ may be measured and analyzed by a commonly used analysis method such as a liquid scintillation counter method, mass spectrometry, infrared spectroscopy, emission spectrometry, or a magnetic resonance spectrum method. Preferably, infrared spectroscopy or mass spectrometry is used.

Steps (1) and (2) of Method (II) calculate the ratio of the $^{13}$CO$_2$ amount to the unlabeled CO$_2$ amount or total CO$_2$ amount in an expired air sample. The proportion of carbon dioxide in an expired air sample may be determined according to a conventional method known to those skilled in the art. An example of such method is described below (see Tsuneo Matsubayashi, Wataru Matsuyama, Society for Medical Application of Carbon Thirteen. 13C-Koki Shiken no Jissai, Kiso to Jissenteki Oyo, Dai 8 Kou: 13C-Koki Shiken Deta Kaisekiho [Practice of 13C-breath tests, basis and practical application, section 8: 13C-breath test data analysis method]. pp. 102-111).

(1) $\delta^{13}$C Value (‰)

Abundances of isotopes are expressed in terms of isotopic ratio (R) in which the most abundant isotope of the same element is used as the denominator. R value for carbon-13 ($^{13}$C) is expressed by the following formula in which carbon-12 ($^{12}$C) is used as the denominator.

$$R = {}^{13}C/{}^{12}C \qquad \text{(Formula 1)}$$

Since R is a very small numerical value, it is difficult to directly measure it. When a mass spectrometer is used for more accurate quantification, comparison with a standard substance is always performed. The measurement result is represented by δ value defined by the following formula.

$$\delta^{13}C = ([R_{SAM}/R_{STD}] - 1) \times 1000 \qquad \text{(Formula 2)}$$

$\delta^{13}$C: $\delta^{13}$C value (‰)
$R_{SAM}$: abundance of $^{13}$C in sample gas
$R_{STD}$: abundance of $^{13}$C in standard gas When carbon dioxide derived from limestone (PDB) is used as standard gas, $R_{STD}$ is $R_{PDB}$=0.0112372.

(2) $\Delta^{13}$C Value (‰)

"$\Delta^{13}$C value (‰)" means a value ($\Delta^{13}$C) obtained by subtracting the $\delta^{13}$C value before administration of a reagent (i.e., naturally occurring δ value of $^{13}$C) as a background from the $\delta^{13}$C value after administration of the reagent, as shown in the following formula.

$$\Delta^{13}C = (\delta^{13}C)t - (\delta^{13}C)0 \qquad \text{(Formula 3)}$$

$\Delta^{13}$C: amount of change in $\delta^{13}$C value (‰)
$(\delta^{13}$C)t: $\delta^{13}$C value at time "t" after reagent administration (‰)
$(\delta^{13}$C)0: $\delta^{13}$C value at time "0" before reagent administration (‰)

(3) $^{13}$C Concentration in Expired Air (%$^{13}$C: atom %)

The $^{13}$C concentration in expired air (%$^{13}$C: atom %) is defined by the following formula.

$$\%^{13}C = [{}^{13}C/({}^{13}C + {}^{12})] \times 100$$

To convert the relative value $\delta^{13}$C defined in (1) into the $^{13}$C concentration (‰) in the total carbon, which is a common concept of concentration, the following method can be used.

First, the numerator and denominator on the right side of the above formula are divided by $^{12}$C, and converted into R based on Formula 1. The following formula is thus obtained.

$$\%^{13}C = [R/(R+1)] \times 100 \qquad \text{(Formula 4)}$$

The following formula is obtained after $R_{SAM}$ obtained in Formula 2 is substituted into R above and the resulting formula is rearranged. The $^{13}$C concentration (%$^{13}$C) can be expressed by using the $\delta^{13}$C value.

$$\%^{13}C = \{([(\delta^{13}C/1000)+1] \times P_{PDB} \times 100\}/\{[[(\delta^{13}C/1000)+1] \times R_{PDB}]+1\} \qquad \text{(Formula 5)}$$

%$^{13}$C: $^{13}$C concentration (atom %)
$\delta^{13}$C: $\delta^{13}$C value (‰)
$R_{PDB}$: abundance of $^{13}$C in PDB standard gas=0.0112372

(4) Amount of Change in $^{13}$C Concentration ($\Delta$%$^{13}$C)

As defined in the following formula, the amount of change in $^{13}$C concentration (%$^{13}$C) in expired air ($\Delta$%$^{13}$C) is determined by subtracting the $^{13}$C concentration at time "0" before administration [(%$^{13}$C)$_0$] from the $^{13}$C concentration at time "t" after administration [(%$^{13}$C)$_t$].

$$\Delta\%^{13}C = (\%^{13}C)_t - (\%^{13}C)_0 \qquad \text{(Formula 6)}$$

$\Delta$%$^{13}$C: amount of change in $^{13}$C concentration (atom %)
(%$^{13}$C)$_t$: $^{13}$C concentration at time "t" after reagent administration (atom %)
(%$^{13}$C)$_0$: $^{13}$C concentration at time "0" before reagent administration (atom %)

(5) Relation Between $\delta^{13}$C Value (‰) and Amount of Change in $^{13}$C Concentration ($\Delta$%$^{13}$C)

The natural abundance (R) of $^{13}$C is about 0.011, and even when a labeled reagent is administered, the increased amount in expired air is only about +0.001 to 0.002. Thus, the natural abundance can be regarded as R→0, and Formula 4, which expresses %$^{13}$C by using R, can be approximated by the following formula.

$$\%^{13}C = [R/(R+1)] \times 100 \approx R \times 100$$

Using this approximate expression, an approximation that determines the $^{13}$C concentration, Formula 7, can be obtained as follows: first, $R_{SAM}$ is determined by Formula 2, which defines $\delta^{13}$C, and substituted into R in the above formula, and the resulting formula is rearranged.

$$\%^{13}C = [(\delta^{13}C/1000)+1] \times R_{PDB} \times 100 \qquad \text{(Formula 7)}$$

When this is substituted into Formula 6, $\Delta^{13}$C can be calculated from $\Delta^{13}$C, as shown in Formula 8 below.

$$\Delta\%^{13}C = (\%^{13}C)_t - (\%^{13}C)_0 \qquad \text{(Formula 8)}$$
$$= \{[(\delta^{13}C)_t - (\delta^{13}C)_0]/1000\} \times R_{PDB} \times 100$$
$$= (\Delta^{13}C \times R_{PDB})/10$$

$\Delta$%$^{13}$C: amount of change in $^{13}$C concentration (atom %)
$\Delta^{13}$C: amount of change in $\delta^{13}$C value (‰)
$R_{PDB}$: abundance of $^{13}$C in PDB standard gas=0.0112372

In steps (1) and (2) of Method (II), the abundance of carbon dioxide contained in the collected expired air (the ratio of the $^{13}$CO$_2$ amount to the unlabeled CO$_2$ amount or total CO$_2$ amount) may be calculated according to the below-described method as the amount of change in $^{13}$C concentration ($\Delta$%$^{13}$C).

More specifically, the $^{13}C$ concentration in total carbon contained in expired air collected at time "t" after administration of the composition to a subject ($^{13}C$ concentration in expired air, $^{13}C$ concentration atom %, $(\%^{13}C)_t$) is determined. Similarly, the $^{13}C$ concentration in total carbon contained in expired air collected in advance before administration, preferably at time "0" before administration, ($^{13}C$ concentration in expired air, $^{13}C$ concentration atom %, $(\%^{13}C)_0$) is determined. Further, $(\%^{13}C)_0$ is subtracted from $(\%^{13}C)_t$ according to Formula 6, thereby obtaining the amount of change in the $^{13}C$ concentration ($\Delta\%^{13}C$ (atom %)).

$$^{13}C \text{ concentration (atom \%)}=[^{13}C/(^{13}C+^{12}C)]\times 100$$

If necessary, the amount of change in the $^{13}C$ concentration ($\Delta\%^{13}C$) may be converted into $\Delta^{13}C$ value (‰) (amount of change in $\delta^{13}C$ value (‰) or DOB (‰)) by Formula 5 and Formula 3.

The ratio of the $^{13}CO_2$ amount to the unlabeled $CO_2$ amount or total $CO_2$ amount in an expired air sample may be expressed as the area under the curve ($AUC_t$) in a graph showing change in $\Delta\%^{13}C$ or $\Delta^{13}C$(‰) over time. The area under the curve may be calculated according to a commonly used method, which would be easily understood by those skilled in the art. For example, the area under the curve is calculated in a graph showing the change in $\Delta\%^{13}C$ or $\Delta^{13}C$(‰) over time, which has the vertical axis showing the $\Delta\%^{13}C$ or $\Delta^{13}C$(‰) and the horizontal axis showing the elapsed time after the administration of $^{13}C$-labeled glucose. For example, $AUC_{t-0}$ may be calculated in the graph, which is the area under the curve from the administration of $^{13}C$-labeled glucose to the expired air collection time "t". For example, $AUC_{t2-t1}$ may be calculated in the graph, which is the area under the curve from the expired air collection time "$t_1$" to the expired air collection time "$t_2$".

Step (3) of Method (II) calculates the difference between the ratio calculated in step (1) and the ratio calculated in step (2). The both ratios may be $\Delta\%^{13}C$, $\Delta^{13}C$(‰), or $AUC_{t-0}$ at the same expired air collection time "t", or $AUC_{t2-t1}$ from the same expired air collection time "$t_1$" to the same expired air collection time "$t_2$". Preferably, the difference of $AUC_{t-0}$ or $AUC_{t2-t1}$ is calculated.

Step (4) of Method (II) evaluates the hepatic glucose uptake capacity based on the difference calculated in step (3). The difference reflects the hepatic glucose uptake capacity of the subject; the larger difference indicates that the proportion of glucose taken up into the liver is larger. Step (4) can comprise comparing the difference with a reference value. The reference value may be derived from the differences calculated according to steps (1) to (3) of Method (II) in a control group, a group of animals of the same species as the subject which have normal hepatic glucose uptake capacities, under the conditions equivalent to those for the subject. The reference value may be obtained simultaneously with, in parallel with, before, or after the measurement of the test value. Alternatively, the reference value may be a value predetermined for each species. Examples of animals having normal hepatic glucose uptake capacities include animals having no metabolic disease, animals in which no abnormality in the liver function is observed by a conventional test method, and animals having no diabetes or pre-onset diabetes such as borderline diabetes. The subject can be determined to have a decreased hepatic glucose uptake capacity when the difference calculated in step (3) is smaller than the reference value. In step (4) of Method (II), the hepatic glucose uptake capacity of the subject can be quantitatively evaluated as the amount or ratio of incorporated glucose by a well-known method.

The hepatic glucose uptake capacity evaluated by Method (II) corresponds to the hepatic extraction ratio calculated from the blood glucose levels in the portal vein, the hepatic vein and the inferior vena cava, as shown in the Examples below. The collection of blood from these blood vessels is inconvenient in actual medical service because it requires advanced technique and puts heavy physical burdens on the subject. Method (II) only requires the intravenous and oral administration in a usual manner in addition to the collection of expired air samples, allowing evaluating the hepatic glucose uptake capacity with a little burden on the subject. Such evaluation can contribute to the treatment and/or prevention of a disease such as a metabolic disease.

An aspect of the disclosure provides a method of evaluating the hepatic glucose uptake capacity of a subject comprising:

(1-1) intravenously administering $^{13}C$-labeled glucose to the subject;
(1-2) obtaining an expired air sample from the subject;
(1-3) calculating the ratio of the $^{13}CO_2$ amount to the unlabeled $CO_2$ amount or total $CO_2$ amount in the sample;
(2-1) orally administering $^{13}C$-labeled glucose to the subject;
(2-2) obtaining an expired air sample from the subject;
(2-3) calculating the ratio of the $^{13}CO_2$ amount to the unlabeled $CO_2$ amount or total $CO_2$ amount in the sample; and
(3) calculating the difference between the ratio calculated in step (1-3) and the ratio calculated in step (2-3); and
(4) evaluating the hepatic glucose uptake capacity based on the difference calculated in step (3).

An aspect of the disclosure provides $^{13}C$-labeled glucose for use in evaluating the hepatic glucose uptake capacity of a subject according to Method (II).

An aspect of the disclosure provides use of $^{13}C$-labeled glucose for manufacturing a composition for evaluating the hepatic glucose uptake capacity of a subject according to Method (II).

Method (III)

The composition comprising $^{13}C$-labeled glucose may be used in Method (III): a method of determining the stage of pre-onset diabetes in a subject with pre-onset diabetes, comprising:

(1) measuring the $^{13}C$-labeled glucose level in a blood sample obtained from the subject to which $^{13}C$-labeled glucose was orally administered; and
(2) comparing the level with a reference value to determine the stage of pre-onset diabetes is stage A or stage B.

As to Method (III), the "subject" may be any mammal. Examples thereof include humans and mammals other than humans. Examples of the mammals other than humans include mice, rats, guinea pigs, rabbits, dogs, cats, monkeys, swine, bovines, and horses, and preferable examples thereof include mice, rats, guinea pigs, rabbits, dogs, and monkeys. In an embodiment, the subject is a human, a rat, or a mouse.

As to Method (III), the term "pre-onset diabetes" means a disease state of diabetes at which the subject has a blood glucose level in a normal range or a little higher, but has a very high blood insulin level or a decreased hepatic glucose uptake capacity. The term pre-onset diabetes also includes borderline diabetes, which is a disease state at which the subject has a blood glucose level higher than the normal range but does not fall within the criteria of diabetes. A subject with pre-onset diabetes has a risk of developing diabetes, unless the lifestyle is improved.

Pre-onset diabetes comprises two stages, stage A and stage B. Stage A is a stage of insulin hypersecretion, and stage B is a stage of a decreased hepatic extraction ratio, namely, a stage of a decreased hepatic glucose uptake capacity. The disease may progress to stage A from stage B, or to stage B from stage A. The blood $^{13}$C-labeled glucose level measured according to Method (III) is low in stage A and high in stage B, as shown in the Examples below. The following table shows the states of parameters at each stage of diabetes.

TABLE 1

|  |  | blood insulin level | blood glucose level | expired air ($\Delta^{13}$C) | blood $^{13}$C-labeled glucose level |
|---|---|---|---|---|---|
| normal |  | → | → | → | → |
| pre-onset | stage A | ↑↑ | →↑ | ↑ | ↓ |
| pre-onset | stage B | ↑↑ | →↑ | ↑ | ↑ |
| early stage diabetes |  | ↑↑ | ↑ | ↓ | ↑ |
| late stage diabetes |  | ↑ | ↑↑ | ↓↓ | ↑↑ |

In the table, symbol → means that the value of each parameter is in a normal range.

Symbol →↑ means that the value of each parameter is in a normal range or a little higher.

Symbol ↑ means that the value of each parameter is higher than a normal range.

Symbol ↑↑ means that the value of each parameter is much higher than a normal range.

Symbol ↓ means that the value of each parameter is lower than a normal range.

Symbol ↓↓ means that the value of each parameter is much lower than a normal range.

The normal ranges of each parameter can be based on the diagnostic criteria for diabetes defined in each country. For example, the normal range of blood glucose level is less than 110 mg/dL on the basis of "Japanese Clinical Practice Guideline for Diabetes 2016", which defines the normal range of the fasting plasma glucose level as "less than 110 mg/dL". Alternatively, the normal ranges can be derived from the values of each parameter measured in a control group, a group of animals of the same species as the subject and having no diabetes or pre-onset diabetes such as borderline diabetes.

Whether a subject has pre-onset diabetes can be determined by any method. For example, the $^{13}CO_2$ amount contained in an expired air after the administration of $^{13}$C-labeled glucose may be used as disclosed in WO2014/030650. For example, such diagnosis can be performed by a method comprising:
(a) calculating the ratio of the $^{13}CO_2$ amount to the unlabeled $CO_2$ amount or total $CO_2$ amount in an expired air sample obtained from the subject to which $^{13}$C-labeled glucose was orally administered;
(b) comparing the ratio with a reference value to evaluate the ability of the subject to metabolize glucose, wherein the reference value is derived from the ratios calculated according to step (a) in animals of the same species which have normal abilities to metabolize glucose; and
(c) determining that the subject has pre-onset diabetes when the ratio is higher than the reference value.

Step (a) can be performed according to step (2) of Method (II). Step (b) compares the ratio calculated in step (a) with a reference value to evaluate glucose metabolism of the subject. The $\Delta\%^{13}C$ or $\Delta^{13}C$ (‰) at a certain time point or the AUC may be used for the comparison. The ratio reflects the ability of the liver of the subject to metabolize glucose; the higher ratio indicates that the ability is better. The reference value may be derived from the ratios calculated according to step (a) in a control group, a group of animals of the same species as the subject which have normal abilities to metabolize glucose, under the conditions equivalent to those for the subject. The reference value may be obtained simultaneously with, in parallel with, before, or after the measurement of the test value. Alternatively, the reference value may be a value predetermined for each species. Examples of animals having normal abilities to metabolize glucose include animals having no metabolic disease, animals in which no abnormality in the liver function is observed by a conventional test method, and animals having no diabetes or pre-onset diabetes such as borderline diabetes. The subject can be determined to have pre-onset diabetes when the ratio calculated in step (a) is higher than the reference value.

Step (1) of Method (III) measures the $^{13}$C-labeled glucose level in a blood sample obtained from the subject to which $^{13}$C-labeled glucose was orally administered. The details of the step are the same as those described for step (1) of Method (I).

Step (2) of Method (III) compares the level with a reference value to determine the stage of pre-onset diabetes is stage A or stage B. The level at a certain time point or the AUC may be used for the comparison. The level reflects the hepatic glucose uptake capacity of the subject; the higher level indicates that the proportion of glucose taken up into the liver is smaller. The reference value may be derived from the levels measured according to step (1) of Method (III) in a control group, a group of animals of the same species as the subject which have normal hepatic glucose uptake capacities, under the conditions equivalent to those for the subject. The reference value may be obtained simultaneously with, in parallel with, before, or after the measurement of the test value. Alternatively, the reference value may be a value predetermined for each species. Examples of animals having normal hepatic glucose uptake capacities include animals not having no metabolic disease, animals in which no abnormality in the liver function is observed by a conventional test method, and animals having no diabetes or pre-onset diabetes such as borderline diabetes. The stage of pre-onset diabetes is determined to be stage A when the level measured in step (1) is lower than the reference value. The stage of pre-onset diabetes is determined to be stage B when the level is higher than the reference value. The stage of pre-onset diabetes is determined to be a transitional stage from stage A to stage B or from stage B to stage A when the level is equivalent to the reference value.

Method (III) enables determining the stage of pre-onset diabetes as demonstrated in Examples below. No method has been available for determining the stage of pre-onset diabetes. Method (III) can contribute to more effective prevention of diabetes.

An aspect of the disclosure provides a method of determining the stage of pre-onset diabetes in a subject with pre-onset diabetes, comprising:
(1) orally administering $^{13}$C-labeled glucose to the subject;
(2) obtaining a blood sample from the subject;
(3) measuring the $^{13}$C-labeled glucose level in the sample; and
(4) comparing the level with a reference value to determine the stage of pre-onset diabetes is stage A or stage B.

An aspect of the disclosure provides a composition comprising $^{13}$C-labeled glucose for determining the stage of pre-onset diabetes in a subject with pre-onset diabetes according to Method (III).

An aspect of the disclosure provides $^{13}$C-labeled glucose for use in determining the stage of pre-onset diabetes in a subject with pre-onset diabetes according to Method (III).

An aspect of the disclosure provides use of $^{13}$C-labeled glucose for manufacturing a composition for determining the stage of pre-onset diabetes in a subject with pre-onset diabetes according to Method (III).

For example, the disclosure provides the following embodiments;

[1] A composition comprising $^{13}$C-labeled glucose for evaluating the hepatic glucose uptake capacity of a subject.

[2] The composition according to item 1, for oral administration.

[3] The composition according to item 1, for intravenous administration.

[4] A method of evaluating the hepatic glucose uptake capacity of a subject, comprising:
(1) measuring the $^{13}$C-labeled glucose level in a blood sample obtained from the subject to which $^{13}$C-labeled glucose was orally administered; and
(2) comparing the level with a reference value to evaluate the hepatic glucose uptake capacity.

[5] The method according to item 4, wherein the reference value is derived from the levels measured according to step (1) in animals of the same species which have normal hepatic glucose uptake capacities.

[6] The method according to item 5, wherein the subject is determined to have a decreased hepatic glucose uptake capacity when the level is higher than the reference value.

[7] A method of evaluating the hepatic glucose uptake capacity of a subject, comprising:
(1) calculating the ratio of the $^{13}CO_2$ amount to the unlabeled $CO_2$ amount or total $CO_2$ amount in an expired air sample obtained from the subject to which $^{13}$C-labeled glucose was intravenously administered;
(2) calculating the ratio of the $^{13}CO_2$ amount to the unlabeled $CO_2$ amount or total $CO_2$ amount in an expired air sample obtained from the subject to which $^{13}$C-labeled glucose was orally administered;
(3) calculating the difference between the ratio calculated in step (1) and the ratio calculated in step (2); and
(4) evaluating the hepatic glucose uptake capacity based on the difference calculated in step (3).

[8] The method according to item 7, wherein step (4) comprises comparing the difference with a reference value, the reference value being derived from the differences calculated according to steps (1) to (3) in animals of the same species which have normal hepatic glucose uptake capacities.

[9] The method according to item 8, wherein the subject is determined to have a decreased hepatic glucose uptake capacity when the difference is smaller than the reference value.

[10] The method according to any one of items 7 to 9, further comprising calculating the amount of hepatic glucose uptake based on the difference calculated in step (3).

[11] A composition comprising $^{13}$C-labeled glucose for determining the stage of pre-onset diabetes in a subject with pre-onset diabetes.

[12] A method of determining the stage of pre-onset diabetes in a subject with pre-onset diabetes, comprising:
(1) measuring the $^{13}$C-labeled glucose level in a blood sample obtained from the subject to which $^{13}$C-labeled glucose was orally administered; and
(2) comparing the level with a reference value to determine the stage of pre-onset diabetes is stage A or stage B.

[13] The method according to item 12, wherein the reference value is derived from the levels measured according to step (1) in animals of the same species which have normal hepatic glucose uptake capacities.

[14] The method according to item 13, wherein the stage is determined to be stage A when the level is lower than the reference value.

[15] The method according to item 14, wherein stage A is the stage of insulin hypersecretion.

[16] The method according to item 13, wherein the stage is determined to be stage B when the level is higher than the reference value.

[17] The method according to item 16, wherein stage B is the stage of decreased hepatic glucose uptake capacity.

[18] The method according to any one of items 12 to 17, wherein the subject is determined to have pre-onset diabetes by a method comprising:
(a) calculating the ratio of the $^{13}CO_2$ amount to the unlabeled $CO_2$ amount or total $CO_2$ amount in an expired air sample obtained from the subject to which $^{13}$C-labeled glucose was orally administered;
(b) comparing the ratio with a reference value to evaluate the ability of the subject to metabolize glucose, wherein the reference value is derived from the ratios calculated according to step (a) in animals of the same species which have normal abilities to metabolize glucose; and
(c) determining that the subject has pre-onset diabetes when the ratio is higher than the reference value.

The entire contents of the documents cited herein are incorporated herein by reference.

The embodiments described above are non-limiting and may be modified without deviating from the scope of the invention as defined by the appended claims. The following example does not restrict or limit the invention and is for illustrative purposes only.

EXAMPLES

Animals

Zucker Diabetic Fatty Rat (ZDF-Lepr$^{fa}$/CrlCrlj) (CHARLES RIVER LABORATORIES JAPAN, INC., Kanagawa, Japan) was used.

ZDF fatty rat, which has a homozygous mutation causing obesity in leptin receptor gene (Lepr$^{fa}$/Lepr$^{fa}$), was used as a model animal for diabetes. The rat develops hyperlipemia and hyperglycemia at the age of about 8 weeks old and develops type 2 diabetes at the age of about 12 weeks old.

ZDF Lean rat, which has a homozygous dominant leptin receptor gene (+/+) or a heterozygote (Lepr$^{fa/+}$), was used as a control for the ZDF fatty rat. The rat has a normal blood glucose level.

Example 1: Evaluation of Hepatic Glucose Uptake Capacity Based on the Blood $^{13}$C Glucose Level and Δ$^{13}$C Value of Expired Air in Rats Having Pre-Onset Diabetes Example 1-1; Evaluation of Hepatic Glucose Uptake Capacity of 6-Week-Old ZDF Fatty Rats To fasted ZDF fatty rats (6 weeks old; n=4) and ZDF lean rats (6 weeks old; n=4) 10 mg/kg of $^{13}C_6$-glucose (13C$_6$-

Glucose [D-GLUCOSE•(U-13C$_6$, 99%)], Cambridge Isotope Laboratories, Inc. (Andover, Mass., USA)) was orally administered. Blood samples and expired air samples were collected over time before and after the administration. The $\Delta^{13}$C values of the obtained expired air samples were measured by GC/MS. The $^{13}$C$_6$-glucose levels in the blood samples were measured by LC/MS/MS. The fasting blood glucose levels were measured before the glucose administration.

The results are shown in FIG. 1. The blood glucose levels of the 6-week-old ZDF fatty rats were 88 mg/dL and the $\Delta^{13}$C values of the expired air samples were kept higher than those of the ZDF lean rats. This indicates the ZDF fatty rats had no diabetes but increased glucose metabolisms, namely, they had pre-onset diabetes. The blood $^{13}$C$_6$ glucose levels of the ZDF fatty rats remained lower than those of the ZDF Lean rats, indicating the hepatic glucose uptake capacities were not decreased in the 6-week old ZDF fatty rats. These results suggest that the 6-week old ZDF fatty rats were in stage A of pre-onset diabetes, i.e., the stage of insulin hypersecretion.

Example 1-2; Evaluation of Hepatic Glucose Uptake Capacity of 7-Week-Old ZDF Fatty Rats To fasted ZDF fatty rats (7 weeks old; n=4) and ZDF lean rats (7 weeks old; n=4) 10 mg/kg of $^{13}$C$_6$-glucose was orally administered. Blood samples and expired air samples were collected over time before and after the administration. The $\Delta^{13}$C values of the obtained expired air samples were measured by GC/MS. The $^{13}$C$_6$-glucose levels in the blood samples were measured by LC/MS/MS. The fasting blood glucose levels were measured before the glucose administration.

Figure 2:
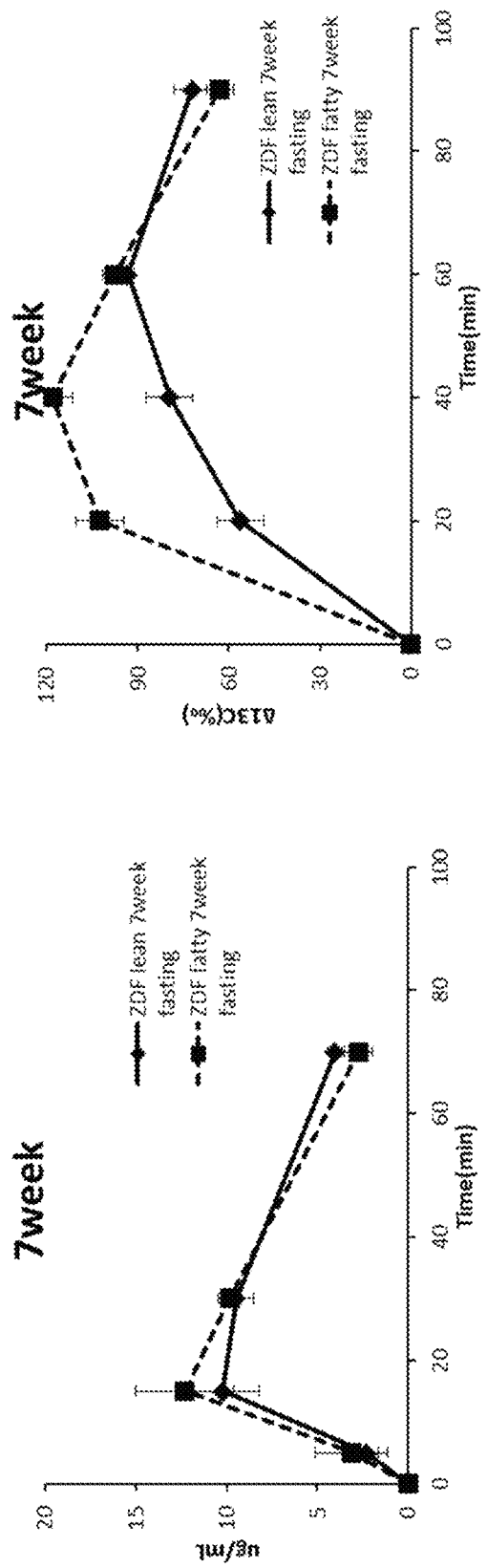
FIG. 2 shows the blood $^{13}C$-glucose levels and the $\Delta^{13}C$ values of the expired air in 7-week-old ZDF fatty rats and ZDF lean rats to which $^{13}C$-glucose was administered.

The results are shown in FIG. 2. The blood glucose levels of the 7-week-old ZDF fatty rats were 88 mg/dL and the $\Delta^{13}$C values of the expired air samples were kept higher than those of the ZDF lean rats. This indicates the ZDF fatty rats had no diabetes but increased glucose metabolisms, namely, they had pre-onset diabetes. The blood $^{13}$C$_6$ glucose levels of the ZDF fatty rats remained higher than those of the ZDF Lean rats, indicating the hepatic glucose uptake capacities were decreased in the 7-week old ZDF fatty rats. These results suggest that the 7-week old ZDF fatty rats were in stage B of pre-onset diabetes, i.e., the stage of decreased hepatic extraction ratio.

Example 1-3; Evaluation of Hepatic Glucose Uptake Capacity of iLIRKO Mice iLIRKO mouse (inducible liver-specific insulin receptor KO mice) can be used as a model for stage B of pre-onset diabetes, the stage of decreased hepatic extraction ratio, because knock out of insulin receptors can be induced only in the liver (Michael M D, et al., Loss of insulin signaling in hepatocytes leads to severe insulin resistance and progressive hepatic dysfunction. Mol Cell 2000; 6 (1): 87-97). To iLIRKO mice (2 to 3 months old, n=5) and IRflox mice (2 to 3 months old, n=5, control) 10 mg/kg of $^{13}$C$_6$-glucose was orally administered. Blood samples and expired air samples were collected over time before and after the administration. The $\Delta^{13}$C values of the obtained expired air samples were measured by GC/MS. The $^{13}$C$_6$-glucose levels in the blood samples were measured by LC/MS/MS.

Figure 3:
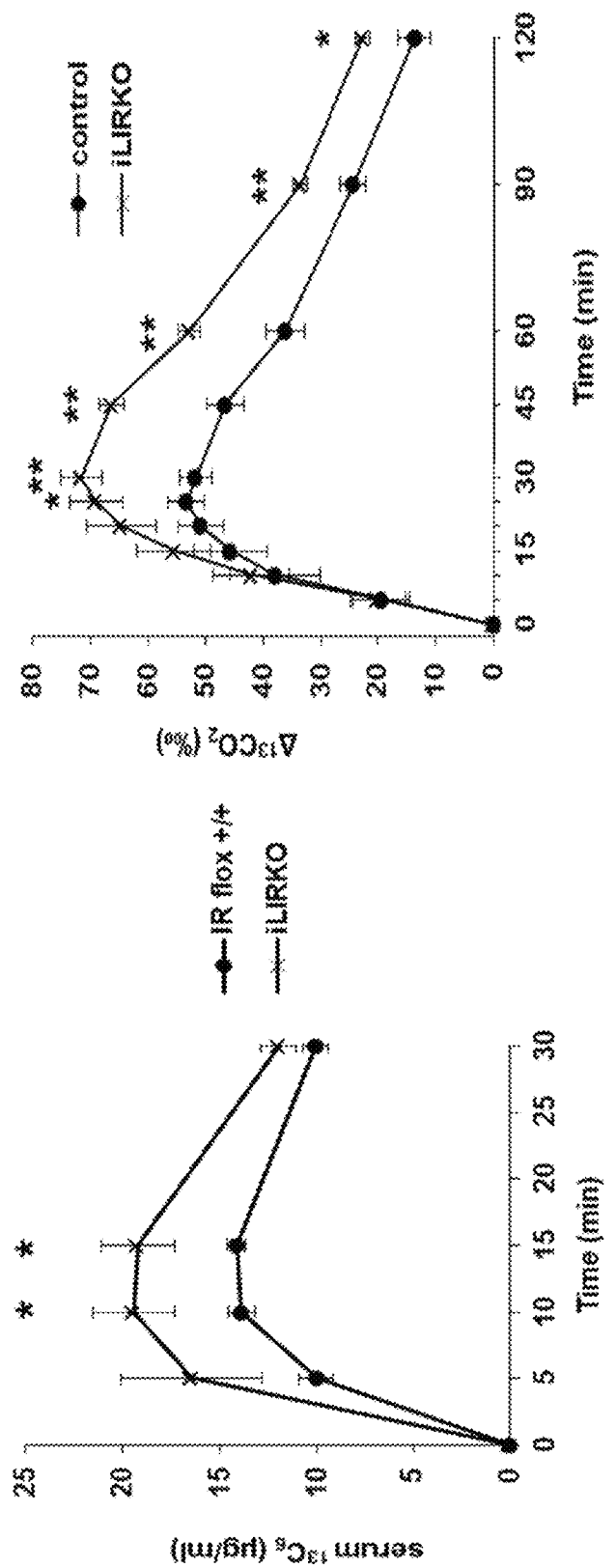
FIG. 3 shows the blood $^{13}C$-glucose levels and the $\Delta^{13}C$ values of the expired air in iLIRKO mice to which $^{13}C$-glucose was administered.

The results are shown in FIG. 3. The $\Delta^{13}$C values of the expired air samples and the blood $^{13}$C$_6$ glucose levels of iLIRKO mice were kept higher than those of IRflox mice. The results agree with the results of Example 1-2. This would be because the normal glucose metabolisms of iLIRKO mice in the organs other than the liver gave the high $\Delta^{13}$C values and the low hepatic glucose uptake capacities gave the high blood $^{13}$C$_6$ glucose levels.

Example 2: Evaluation of Glucose Uptake Capacity Based on the $\Delta^{13}$C Value of Expired Air after IV and PO Administration of $^{13}$C-Labeled Glucose

Example 2-1: $\Delta^{13}$C Value of Expired Air after IV and PO Administration of $^{13}$C-Labeled Glucose To unfasted ZDF fatty rats (18 weeks old; n=6), ZDF lean rats (18 weeks old; n=6) and SD rats (14 weeks old; n=3) 10 mg/kg of $^{13}$C$_6$-glucose was orally administered. Expired air samples were collected over time before and after the administration and the $\Delta^{13}$C values of the samples were measured by GC/MS. Three days after the oral administration, 10 mg/kg of $^{13}$C$_6$-glucose was intravenously administered to the same unfasted rats. Expired air samples were collected over time before and after the administration and the $\Delta^{13}$C values of the samples were measured by GC/MS.

Figure 4:
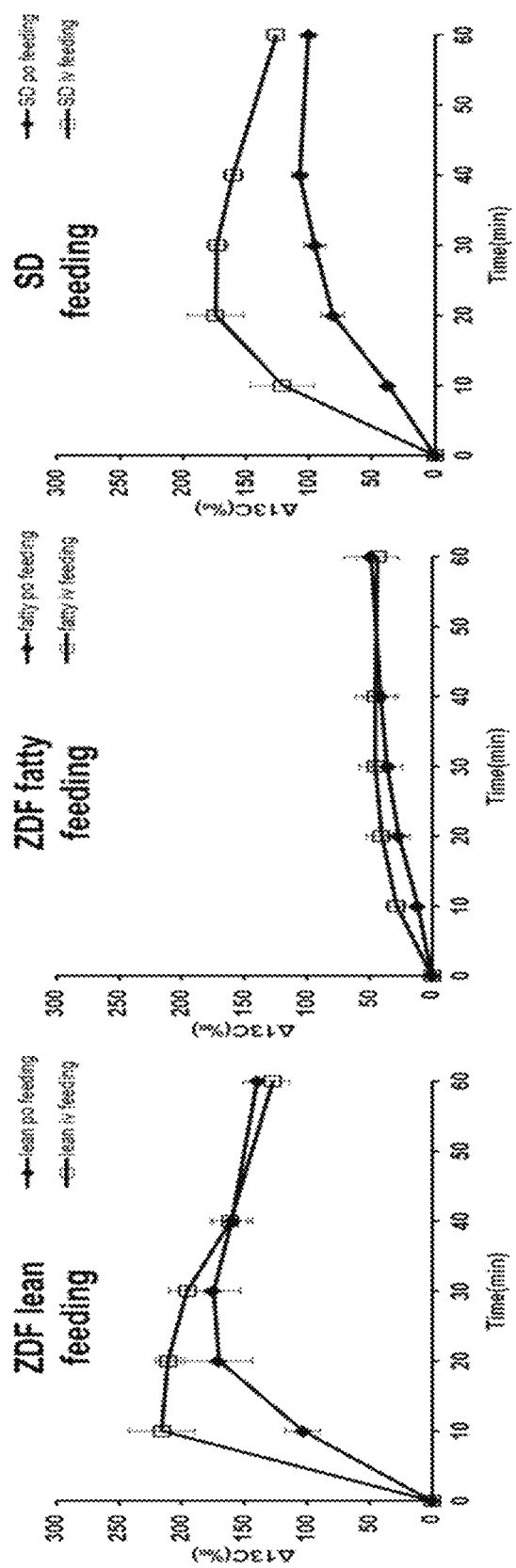
FIG. 4 shows the $\Delta^{13}C$ values of the expired air in ZDF fatty rats, ZDF lean rats, and SD rats to which $^{13}C$-glucose was administered orally or intravenously.

The results are shown in FIG. 4. In the ZDF fatty rats, a model for diabetes, little difference was found between the $\Delta^{13}$C values after the oral administration and the $\Delta^{13}$C values after the intravenous administration, whereas in the both of ZDF lean rats and SD rats, controls, some difference was found; the $\Delta^{13}$C values after the intravenous administration were higher. The difference in the $\Delta^{13}$C values is thought to reflect the hepatic glucose uptake capacity because orally administered glucose passes through the liver but intravenously administered glucose does not.

Figure 5:
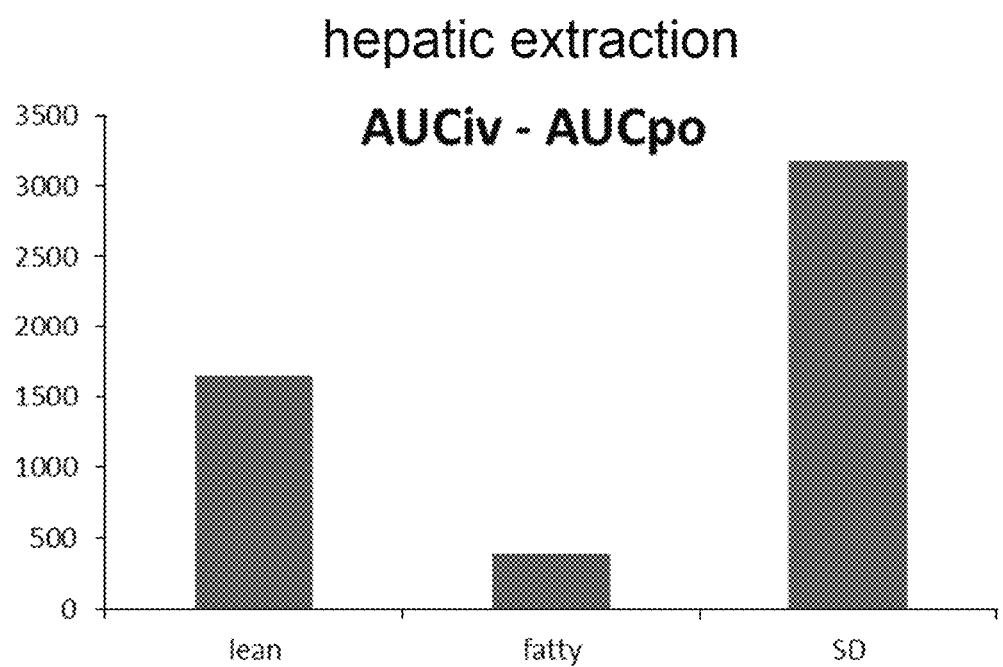
FIG. 5 shows the amount of the hepatic glucose uptake (hepatic extraction) determined by calculating the AUCs of the $\Delta^{13}C$ values shown in FIG. 4 and calculating the difference of the AUCs between the oral administration and the intravenous administration.

The AUCs of the $\Delta^{13}$C values were calculated for the oral administration and the intravenous administration, and the difference of the AUCs was calculated. The difference is shown in FIG. 5 as the amount of hepatic glucose uptake (hepatic extraction). The graph shows the amount was high in order of the SD rats, the ZDF lean rats, and the ZDF fatty rats, indicating that the amount of hepatic extraction is low in the ZDF fatty rats, a model for diabetes. The amount of hepatic extraction of the ZDF lean rats, which have the heterozygous mutation in leptin gene, was lower than that of the SD rats, which do not have the mutation. The mutation is homozygous in the ZDF fatty rats.

Figure 6:
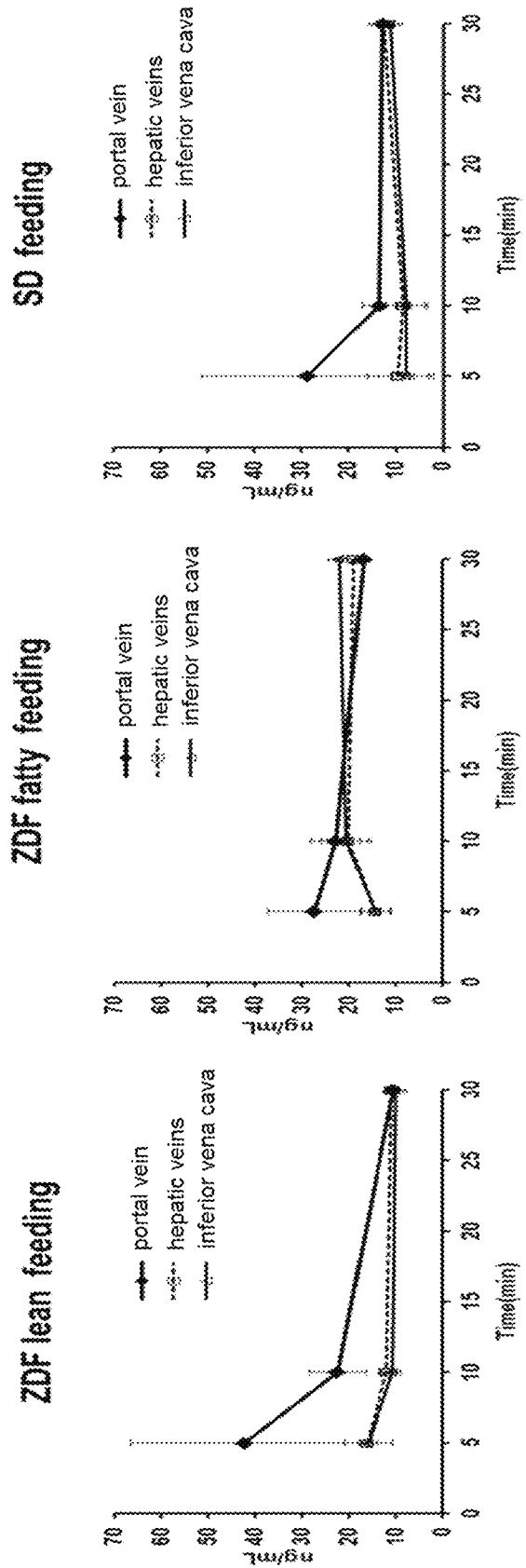
FIG. 6 shows the $^{13}C$-glucose levels in blood samples collected from the portal vein, the hepatic veins and the inferior vena cava of ZDF fatty rats, ZDF lean rats and SD rats to which $^{13}C$-glucose was orally administered.

Example 2-2: Measurement of Hepatic Extraction Ratio Based on Blood $^{13}$C-Labeled Glucose Level To unfasted rats (ZDF lean, ZDF fatty, SD, each n=12) 10 mg/kg of $^{13}$C$_6$-glucose was orally administered. Four rats of each group were euthanized and subjected to laparotomy 5 minutes, 10 minutes, and 30 minutes after the administration, and blood was collected simultaneously from the portal vein, the hepatic veins, and the inferior vena cava. The blood $^{13}$C$_6$-glucose level was measured by LC/MS/MS. The results are shown in FIG. 6. When the blood samples were collected 5 minutes or 10 minutes after the glucose administration, the levels were high in order of the portal vein, the hepatic veins, and the inferior vena cava in all the rats.

Figure 8:
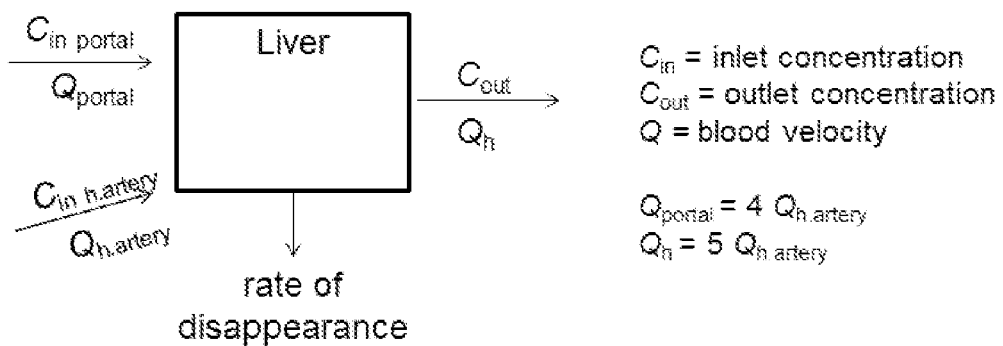
FIG. 8 shows the formulae for calculating the hepatic extraction ratio of $^{13}C_6$-glucose from the measured levels.

The hepatic extraction ratio of $^{13}$C$_6$-glucose was calculated from the measured levels using the formulae shown in FIG. 8.

Figure 7:
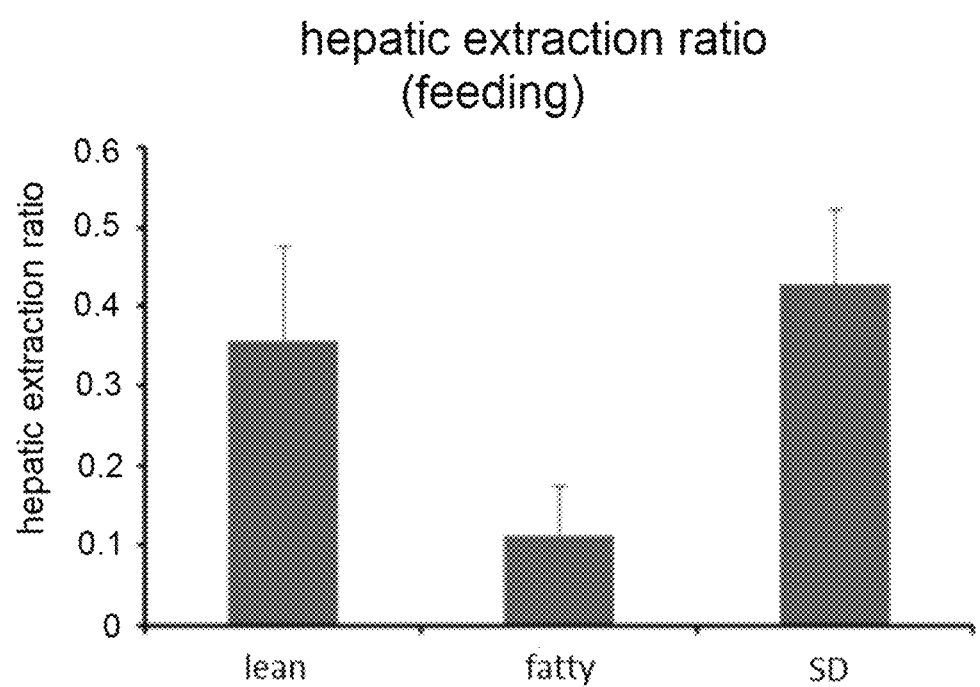
FIG. 7 shows the hepatic extraction ratios of $^{13}C$-glucose which were calculated from the results shown in FIG. 6.

The results are shown in FIG. 7. The hepatic extraction ratio was high in order of the SD rats, the ZDF lean rats, and the ZDF fatty rats. The results agree with the results of Example 2-1, demonstrating the glucose uptake capacity evaluated in Example 2-1, which is based on the $\Delta^{13}C$ values of the expired air after the oral and intravenous administration of $^{13}C$-glucose, corresponds to the actual hepatic extraction ratio.

INDUSTRIAL APPLICABILITY

The disclosure enables evaluating the hepatic glucose uptake capacity of a subject. Such evaluation can facilitate diagnosis of metabolic diseases, e.g., diabetes, and can contribute to preventive medicine. Enhancing prevention of metabolic diseases for suitable subjects is advantageous for medical economy.

What is claimed is:

1. A method of determining the stage of pre-onset diabetes in a subject, comprising:
    (1-1) orally administering $^{13}C$-labeled glucose to the subject;
    (1-2) obtaining an expired air sample from the subject;
    (1-3) calculating the ratio of the $^{13}CO_2$ amount to the unlabeled $CO_2$ amount or total $CO_2$ amount in the sample;
    (1-4) comparing the ratio with a reference value;
    (1-5) determining that the subject has pre-onset diabetes when the ratio is higher than the reference value;
    (2-1) orally administering $^{13}C$-labeled glucose to the subject who has been determined to have pre-onset diabetes in step (1-5);
    (2-2) obtaining a blood sample from the subject;
    (2-3) measuring the $^{13}C$-labeled glucose level in the blood sample; and
    (2-4) comparing the level with a reference value to determine the stage of pre-onset diabetes is a stage of insulin hypersecretion or a stage of decreased hepatic glucose uptake capacity.

2. The method according to claim 1, wherein the reference value in step (2-4) is obtained by performing steps (2-1) through (2-3) in control animals which have normal hepatic glucose uptake capacities.

3. The method according to claim 2, wherein the stage is determined to be the stage of insulin hypersecretion when the level is lower than the reference value in step (2-4).

4. The method according to claim 2, wherein the stage is determined to be the stage of decreased hepatic glucose uptake capacity when the level is higher than the reference value in step (2-4).

5. The method according to claim 1, wherein the reference value in step (1-4) is obtained by performing steps (1-1) through (1-3) in control animals which have normal abilities to metabolize glucose.

6. A method of determining the stage of pre-onset diabetes in a subject, comprising:
    (1) orally administering $^{13}C$-labeled glucose to the subject;
    (2-1) obtaining an expired air sample from the subject of step (1);
    (2-2) calculating the ratio of the $^{13}CO_2$ amount to the unlabeled $CO_2$ amount or total $CO_2$ amount in the sample;
    (2-3) comparing the ratio with a reference value;
    (2-4) determining that the subject has pre-onset diabetes when the ratio is higher than the reference value;
    (3-1) obtaining a blood sample from the subject of step (1);
    (3-2) measuring the $^{13}C$-labeled glucose level in the blood sample; and
    (3-3) comparing the level with a reference value to determine the stage of pre-onset diabetes is a stage of insulin hypersecretion or a stage of decreased hepatic glucose uptake capacity.

7. The method according to claim 6, wherein the reference value in step (3-3) is obtained by performing steps (1), (3-1) and (3-2) in control animals which have normal hepatic glucose uptake capacities.

8. The method according to claim 7, wherein the stage is determined to be the stage of insulin hypersecretion when the level is lower than the reference value in step (3-3).

9. The method according to claim 7, wherein the stage is determined to be the stage of decreased hepatic glucose uptake capacity when the level is higher than the reference value in step (3-3).

10. The method according to claim 6, wherein the reference value in step (2-3) is obtained by performing steps (1), (2-1) and (2-2) in control animals which have normal abilities to metabolize glucose.

* * * * *